United States Patent
Bregman-Amitai et al.

(10) Patent No.: US 9,940,711 B2
(45) Date of Patent: Apr. 10, 2018

(54) SYSTEMS AND METHODS FOR DETECTING A FATTY LIVER FROM A COMPUTED TOMOGRAPHY (CT) SCAN

(71) Applicant: Zebra Medical Vision Ltd., Ramat-HaSharon (IL)

(72) Inventors: Orna Bregman-Amitai, Tel-Aviv (IL); Eldad Elnekave, Tel-Aviv (IL)

(73) Assignee: Zebra Medical Vision Ltd., Shefayim (IL)

( * ) Notice: Subject to any disclaimer, the term of this patent is extended or adjusted under 35 U.S.C. 154(b) by 15 days.

(21) Appl. No.: 15/264,766

(22) Filed: Sep. 14, 2016

(65) Prior Publication Data
US 2017/0148156 A1 May 25, 2017

Related U.S. Application Data

(60) Provisional application No. 62/259,746, filed on Nov. 25, 2015.

(51) Int. Cl.
| | |
|---|---|
| G06K 9/00 | (2006.01) |
| G06T 7/00 | (2017.01) |
| A61B 6/03 | (2006.01) |
| A61B 6/00 | (2006.01) |
| G06T 7/11 | (2017.01) |
| G06T 7/136 | (2017.01) |

(52) U.S. Cl.
CPC .......... *G06T 7/0012* (2013.01); *A61B 6/032* (2013.01); *A61B 6/461* (2013.01); *A61B 6/481* (2013.01); *A61B 6/50* (2013.01); *A61B 6/5217* (2013.01); *G06T 7/11* (2017.01); *G06T 7/136* (2017.01); *G06T 2207/10081* (2013.01); *G06T 2207/20036* (2013.01); *G06T 2207/30056* (2013.01)

(58) Field of Classification Search
CPC ... G06T 7/0012; G06T 7/0081; G06T 11/003; G06T 2207/0081; G06T 2207/30056; A61B 6/032; A61B 6/0306; A61B 6/50; A61B 6/5217; A61B 6/481; A61B 6/461
See application file for complete search history.

(56) References Cited

U.S. PATENT DOCUMENTS

| | | | |
|---|---|---|---|
| 6,999,549 B2 | 2/2006 | Sabol et al. | |
| 8,983,571 B2 | 3/2015 | Davis et al. | |
| 9,036,883 B2 | 5/2015 | Su et al. | |
| 2003/0179915 A1* | 9/2003 | Goto | A61B 6/463 382/128 |
| 2004/0101086 A1 | 5/2004 | Sabol et al. | |

(Continued)

*Primary Examiner* — Amir Alavi

(57) ABSTRACT

There is provided a computer-implemented method for detecting a fatty liver, comprising: receiving imaging data of a computed tomography (CT) scan performed using a single source CT Scanner with settings selected for imaging of non-fatty-liver pathology, segmenting a region of the liver by creating a binary image by applying binary segmentation to a sub-set of pixels of the imaging data according to a first set-of-rules, and mapping the region of liver of the binary image to the segmented region of the portion of the liver of the imaging data, calculating liver parameter(s) for the segmented region of the liver from Hounsfield unit (HU) value(s), and detecting the presence of a fatty liver by analyzing the calculated liver parameter(s) according to a second set-of-rules.

24 Claims, 8 Drawing Sheets

(56) References Cited

U.S. PATENT DOCUMENTS

| | | | |
|---|---|---|---|
| 2008/0008366 A1* | 1/2008 | Desh | G06T 19/00 |
| | | | 382/128 |
| 2008/0310717 A1* | 12/2008 | Saathoff | G06K 9/342 |
| | | | 382/173 |
| 2009/0185731 A1* | 7/2009 | Ray | G06T 7/0012 |
| | | | 382/131 |
| 2009/0226060 A1* | 9/2009 | Gering | G06T 7/11 |
| | | | 382/128 |
| 2010/0030064 A1* | 2/2010 | Averbuch | A61B 6/032 |
| | | | 600/424 |
| 2016/0328631 A1* | 11/2016 | Lay | G06K 9/6267 |
| 2017/0148156 A1* | 5/2017 | Bregman-Amitai | G06T 7/0012 |
| 2017/0263009 A1* | 9/2017 | Averbuch | A61B 6/032 |

* cited by examiner

`US 9,940,711 B2`

SYSTEMS AND METHODS FOR DETECTING A FATTY LIVER FROM A COMPUTED TOMOGRAPHY (CT) SCAN

RELATED APPLICATION

This application claims the benefit of priority under 35 USC § 119(e) of U.S. Provisional Patent Application No. 62/259,746 filed Nov. 25, 2015, the contents of which are incorporated herein by reference in their entirety.

FIELD AND BACKGROUND OF THE INVENTION

The present invention, in some embodiments thereof, relates to a systems and methods for analyzing computed tomography (CT) scans and, more specifically, but not exclusively, to systems and methods for detecting a fatty liver from a CT scan.

Fatty Liver, also termed Hepatic Steatosis, is relatively common. Studies report a rate of 11.4% of the adult population in the United States, and in particular, a rate of 22% among diabetic patients.

Fatty liver has been traditionally linked to alcohol consumption, and in some cases appears in patients that do not consume alcohol (e.g., nonalcoholic steatohepatitis (NASH)). However, recent studies suggest that fatty liver is a risk factor for several key preventable diseases. For example, studies suggest that the presence of fatty liver in a person that seams otherwise healthy is associated with subclinical cardiovascular changes, elevated inflammatory markers of atherosclerosis and heart dysfunction. In patients with medical conditions, for example diabetics (type II), studies suggest that fatty liver is associated with coronary artery disease (after adjusting for confounding factors like age, gender, obesity, hypertension, smoking status and low density lipoprotein LDL).

Studies suggest that fatty liver is independently associated with increased coronary artery calcification, and that fatty liver is a strong predictor of high risk coronary artery plaque. In particular, the presence of fatty liver increases the risk for having high risk coronary artery plaque by 2.13-4.6×. In another study, people with fatty liver were nearly two times as likely to experience a cardiovascular event (i.e., heart attack or sudden death) over a mean follow up interval of 7.3 years.

SUMMARY OF THE INVENTION

According to an aspect of some embodiments of the present invention, there is provided a computer-implemented method for detecting a fatty liver from CT imaging data, comprising: receiving imaging data of a computed tomography (CT) scan of a body of a patient including at least a portion of a liver, the CT scan performed using a single source CT Scanner with settings selected for imaging of non-fatty-liver pathology; segmenting at least a region of the portion of the liver from the imaging data by creating a binary image by applying binary segmentation to a sub-set of pixels of the imaging data according to a first set-of-rules, wherein the binary image includes the region of the portion of the liver, and mapping the region of the portion of the liver of the binary image to the segmented region of the portion of the liver of the imaging data; calculating at least one liver parameter for the segmented region of the liver from Hounsfield unit (HU) value(s); detecting the presence of a fatty liver by analyzing the calculated at least one liver parameter according to a second set-of-rules; and outputting an indication of the presence of the fatty liver.

Optionally, the method further comprises calculating a probability of correctly identifying the presence of the fatty liver, and outputting the probability in association with the indication.

Optionally, the method further comprises calculating a confidence grade of correctly segmenting at least one of the liver region and a spleen region.

Optionally, the method further comprises identifying that the imaging data is associated with a non-contrast CT (NCCT) scan or a venous phase of a contrast enhanced CT (CECT) scan; segmenting a region of a spleen from the imaging data; calculating at least one spleen parameter for the segmented region of the spleen; and detecting the presence of the fatty liver by analyzing the calculated at least one liver parameter in view of the calculated at least one spleen parameter according to the second set-of-rules.

Optionally, the second set-of-rules comprises detecting the fatty liver when the at least one liver parameter includes an average HU at least 10 HU below the at least one spleen parameter including an average of HU values.

Optionally, the imaging data associated with non-contrast or contrast enhanced and the vascular phase of contrast identified as arterial or venous is retrieved from a respective DICOM field of a file storing the imaging data. Alternatively or additionally, the imaging data associated with non-contrast or contrast enhanced and the vascular phase of contrast identified as arterial or venous is retrieved using an automatic analysis of the DICOM images. Alternatively or additionally, the imaging data associated with non-contrast or contrast enhanced and the vascular phase of contrast identified as arterial or venous is received as manually entered input.

Optionally, segmenting the region of the spleen further comprises excluding tissues of other nearby organs from the segmentation. Optionally, the method further comprises designating an axial slice at which the liver region has been segmented from a set of sequentially organized axial slices of the imaging data; and wherein segmenting comprises segmenting the region of the spleen from the designated axial slice. Optionally, the method further comprises defining an ROI within the designated axial slice positioned mostly posterior and within the left side of the patient creating a binary image based on the ROI by applying binary segmentation to the pixels of the ROI according to at least one of: predefined HU values when the imaging data is associated with CT image acquisition, and relative to the calculation of least one liver parameter; and mapping the region of the spleen within the image data according to corresponding pixels in the binary image. Optionally, the method further comprises pre-processing the binary image by at least one of erosion and dilation; connecting components of the binary image according to a first connection set-of-rules; validating the largest component according to a second connection set-of-rules; and mapping the region of the spleen according to the largest component.

Optionally, the second set-of-rules comprise detecting the fatty liver when the at least one liver parameter is below a threshold of 40 HU.

Optionally, segmenting the portion of the liver comprises segmenting tissue of the portion of the liver and excluding blood vessels from the segmentation according to a blood vessel size requirement.

Optionally, segmenting comprises segmenting the region within the right posterior sector (RPS), and wherein calculating comprises calculating the at least one liver parameter for the segmented region of the RPS.

Optionally, the method further comprises building a volume from the imaging data using a predefined size for voxels, and segmenting comprises segmenting the region from the volume.

Optionally, the method further comprises identifying an axial slice having the largest lung area from a set of sequentially organized axial slices of the imaging data, and searching for the liver region in respective sequential axial slices starting from the identified axial slice in an inferior direction. Optionally, the search is performed within a region of interest (ROI) positioned mostly posterior and within the right side of the patient. Optionally, the method further comprises, for each respective axial slice in the sequence: identifying a body portion of the patient; eroding the body portion until the ribs or until an erosion distance from the ribs; defining the ROI within the respective axial slice; segmenting the lungs within the ROI according to HU values of pixels according to a lung requirement; and identifying the region of the liver when the area of the segmented lung in the ROI is according to a liver area requirement.

Optionally, identifying the region of the liver further comprises: calculating a histogram based on the HU values of pixels in the ROI; creating a binary image based on the ROI by applying binary segmentation to the pixels of the ROI according to the value of the bin of the histogram having the greatest value; and mapping the region of the liver within the image data according to corresponding pixels in the binary image.

Optionally, mapping further comprises mapping the region of the liver based on the binary image such that the region is located a distance from the edge of the liver, within the liver.

According to an aspect of some embodiments of the present invention, there is provided a system for detecting a fatty liver from CT imaging data, comprising: an imaging interface for receiving imaging data of a CT scan of a body of a patient including at least a portion of a liver acquired by a single source CT scanner with settings selected for imaging of non-fatty liver pathology; a communication interface for communicating with an external device; a program store storing code; and a processor coupled to the imaging interface, the communication interface, and the program store for implementing the stored code, the code comprising: code to receive, using the imaging interface, imaging data of a computed tomography (CT) scan of a body of a patient including at least a portion of a liver; code to segment at least a region of the portion of the liver from the imaging data, by creating a binary image by applying binary segmentation to a sub-set of pixels of the imaging data according to a first set-of-rules, wherein the binary image includes the region of the portion of the liver, and mapping the region of the portion of the liver of the binary image to the segmented region of the portion of the liver of the imaging data; code to calculate at least one liver parameter for the segmented region of the liver based on HU values, detect the presence of a fatty liver by analyzing the at least one calculated liver parameter according to a second set-of-rules; and code to output an indication of the presence of the fatty liver using the communication interface.

Optionally, the system further comprises code to mark the segmented region on a respective axial slice of the imaging data, and code to output the respective axial slice for presentation on a display.

According to an aspect of some embodiments of the present invention, there is provided a computer program product comprising a non-transitory computer readable storage medium storing program code thereon for implementation by a processor of a computing unit that detects a fatty liver from CT imaging data, the program code comprising: instructions to receive imaging data of a computed tomography (CT) scan of a body of a patient including at least a portion of a liver, the CT scan performed using a single source CT Scanner with settings selected for imaging of non-fatty-liver pathology; instructions to segment at least a region of the portion of the liver from the imaging data by creating a binary image by applying binary segmentation to a sub-set of pixels of the imaging data according to a first set-of-rules, wherein the binary image includes the region of the portion of the liver, and mapping the region of the portion of the liver of the binary image to the segmented region of the portion of the liver of the imaging data; instructions to calculate at least one liver parameter for the segmented region of the liver based on HU values; instructions to detect the presence of a fatty liver by analyzing the calculated at least one liver parameter according to a second set-of-rules; and instructions to output an indication of the presence of the fatty liver.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
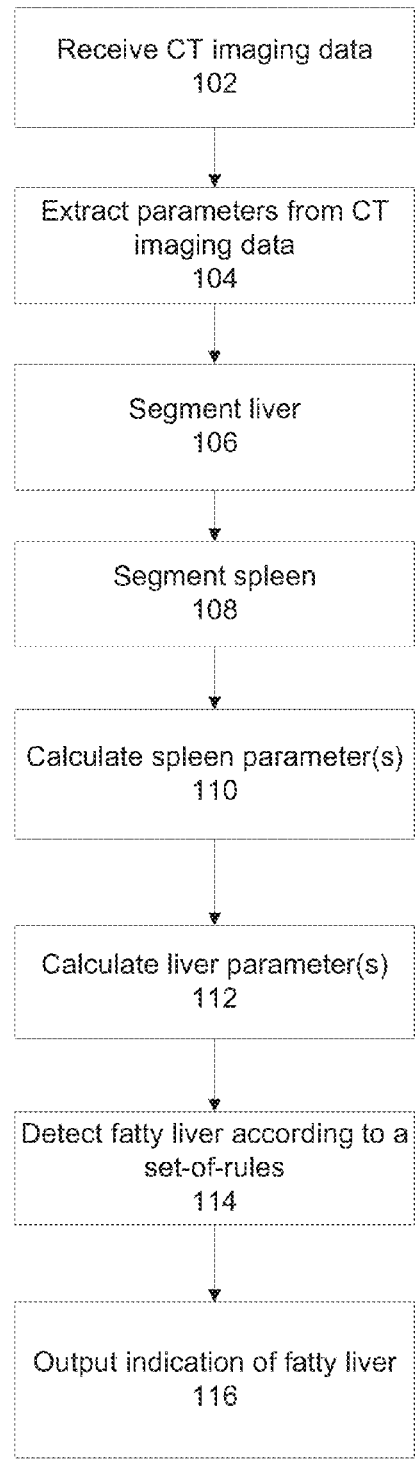
FIG. 1 is a flowchart of a computer-implemented method that automatically detects a fatty liver from CT imaging data, in accordance with some embodiments of the present invention.

The present invention, in some embodiments thereof, relates to a systems and methods for analyzing computed tomography (CT) scans and, more specifically, but not exclusively, to systems and methods for detecting a fatty liver from a CT scan.

An aspect of some embodiments of the present invention relates to systems and/or methods (e.g., code instructions stored in a program store implementable by a processor) that automatically process imaging data acquired by a single source CT scanner scanning a patient and identify a fatty liver (or relatively high probability of fatty liver) by automatically segmenting the fatty liver based on a created binary image. A region of the liver, optionally located within the right posterior sector (RPS) of the liver is automatically identified and segmented using the binary image. Liver parameter(s) are calculated for the segmented region. The liver parameter(s) may be calculated based on Hounsfield units (HU), optionally the average HU of pixels within the segmented region. The fatty liver is detected by analyzing the liver parameter(s) by applying a set-of-rules. The automated method may be performed on one or more, optionally a corpus of CT scans, without requiring a radiologist to manually review each CT scan, for example, as a by-the-way analysis.

Optionally, the CT scan analyzed for the presence of fatty liver is acquired using a single source CT scanner, or for example, a dual-source CT (or multi-source CT) in which both (or all) x-ray sources work at the same setting (e.g., same kilo-Volt (kV) setting). The CT scan may be performed using routine imaging examination CT scanning protocols, and/or using settings selected for imaging of non-fatty-liver pathology (i.e., selected for diagnosis of conditions other than fatty liver).

The CT scan may be acquired using non-fatty-liver detection protocols and/or devices, for example, without special energy settings (e.g., using a single source setting instead of for example, multi-source CT using different kV settings for each x-ray source). The CT scan may be a standard scan for non-fatty-liver indications, for example, a chest CT scan, and an abdominal CT scan.

Optionally, the liver (and/or the spleen) parameter (e.g., average intensity) may be associated with a confidence grade that may give information about the quality of the measurement. The confidence grade may affect the confidence of the fatty liver detection results. The confidence grade may be used to flag or un-flag the need for additional investigation, for example, using a confidence requirement such as a threshold or range.

Optionally, the fatty liver diagnosis and/or detected indication may be associated with a probability according to the diagnostic scheme used by the algorithm.

Optionally, the binary image is created based on a region of interest (ROI) identified as including at least a portion of the liver, optionally the RPS. The binary image is created by applying binary segmentation to the pixels in the ROI. The region of the liver may be identified from the binary image (e.g., represented by pixels having one of the binary values), and mapped back to the imaging data.

Optionally, the segmentation of the liver region is performed on one or more selected axial slices selected from a set of sequential axial slices of the CT scan. The axial slices are selected by analyzing the relative area of lung volume and liver tissue within the ROI of the respective axial slice according to a liver area requirement (e.g., area of liver larger than area of lung).

Optionally, the fatty liver is detected by analyzing the liver parameter(s) in view of spleen parameter(s) (optionally based on HU values, optionally an average HU value of pixels in the segmented spleen) calculated for a region of the spleen. The region of the spleen may be automatically segmented in imaging data automatically identified as performed using a non-contrast CT (NCCT) scan, or a venous phase of a contrast enhanced CT (CECT) scan (which may be detected by accessing a field of a DICOM file storing the imaging data of the CT scan).

The region of the spleen may be identified from a binary image created based on a ROI identified as including a portion of the spleen in a selected axial slice. The selected axial slice may be the same slice in which the liver is identified. The binary segmentation of the ROI that includes the spleen may be performed according to predefined values when the CT scan has been acquired using NCCT, and/or relative to the liver parameter(s).

Optionally, the segmented liver region and/or the segmented spleen region is designated to respectively include pixels representing liver tissue and spleen tissue.

Optionally, pixels representing blood vessels (e.g., large blood vessels), tumors, malformations, and other nearby organs and/or tissues are excluded from the segmented region(s).

The systems and/or methods described herein provide a technical solution to the technical problem of automatically improving digital images stored as CT imaging data, which may be acquired for different parts of the body using different acquisition protocols. The technical problem may relate to automatically determining whether the CT imaging data includes (e.g., with a probability level defined according to a probability requirement) a fatty liver. The technical problem may relate to automatically segmenting a region of the liver and optionally the spleen for use in calculating a value used in the process of identifying fatty liver.

The systems and/or methods described herein tie mathematical operations (e.g., segmentation, calculation of HU values) to the ability of a processor to process digital images, for example, by creating a binary image, and mapping the liver and/or spleen represented within the binary image to the CT imaging data.

The systems and/or methods described herein relate to processing CT imaging data stored in a physical storage device. A graphical user interface (GUI) may present the results of the processing on a physical display, for example, by marking the CT imaging data with the segmented region of the liver (and optionally the spleen) used to calculate the liver parameter for identifying the fatty liver. New data may be created in the form of the generated indication of the presence (or probability of the presence) of fatty liver in the CT imaging data, which may be stored in associated with the CT imaging data, for example, as a field in a DICOM file storing the CT imaging data. New data may be created in the form of one or more binary images used to segment the liver and/or spleen. New data may be created in the form of an enhancement of the CT imaging data, by marking the segmented region of the liver (and optionally the spleen) on the CT imaging data, for presentation on the GUI.

The systems and/or methods described herein improve performance of computer(s) (e.g., client terminal, servers) and/or network, for example, by using less memory and/or improving computation time in producing an improved digital image.

Accordingly, the systems and/or methods described herein are necessarily rooted in computer technology to overcome an actual technical problem arising in digital image processing.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms pixels and voxels are sometimes interchangeable, for example, in reference to segmentation and/or calculation of liver parameter(s) and/or calculation of spleen parameter(s).

As used herein, the term segment or segmentation means a region of the liver or spleen, which may be defined by the ROI, identified for calculation of the liver parameter and/or spleen parameter. It is noted that the segment may include the suitable identified region of the liver and/or spleen for calculation of the liver and/or spleen parameter, rather than, for example, including the entire visible liver and/or spleen.

As used herein, the term Confidence grade means the accuracy of the detection and/or the evaluation of the segmented liver (and optionally the segmented spleen) intensity, optionally the average intensity. The scale may be, for example, 0-1, 0-100 or other predefined scale.

The confidence grade may be calculated using one or more exemplary methods (e.g., using code stored in a program store implementable by a processor, as described here):
  Calculated during the liver and/or spleen segmentation (e.g., as described with reference to FIG. 3 and/or FIG. 4) based on parameters of the image and/or the segmentation process. For example, one or more of:
  Standard deviation (std) of the segmented area.
  The ratio between the std of the organ and the std of another organ.
  The smoothness of the edges of the organ.
  The curvature of its posterior edges.
  Shape similarity to a healthy organ shape, for example, the similarity of the spleen to banana shape.
  The intensity difference from the environment.
  The organ size normalized by patient axial body section.
  Function of the CT scan technical parameters.
  Function based on one or more of the parameters (e.g., average, weighted average, multiplication).
  Based on off-line statistics and/or validation of large scale population, for example:
  Different for liver and for spleen.
  Fixed for all—for example, 95% if validation showed that detection has 5% of error for all cases.
  Dependent on the intensity—if errors were found during validation more or less for different intensity range.
  Dependent on contrast/non-contrast.
  Other CT scan parameters—for example, resolution, dose, protocol, manufacture.
  Dependent on demographic information—for example, age, gender.
  Other dependencies.
  Combination of the parameters (e.g., average, weighted average, multiplication).
  Combination of the segmentation process parameters and the off-line statistics.

As used herein, the phase Probability of fatty liver means the probability that the segmentation output parameters indicate that patient has a fatty liver, optionally due to any underlying cause. This probability may be based on predefined parameters obtained, for example, from research studies.

In a not necessarily limiting example, an implementation uses a diagnostic scheme (i.e., set-of-rules) of >95% probability for fatty liver in cases where the average intensity of the liver is below 40 HU or the liver average intensity is less by 10 HU or more from the spleen and the scan was non-contrast or contrast enhanced in the venous phase. In other cases the probability of fatty liver may remain unknown.

The probability of fatty liver may be calculated according to other input, for example, demographic information, exposure to toxins such as chemotherapy and underlying metabolic disease such as diabetes.

Figure 2:
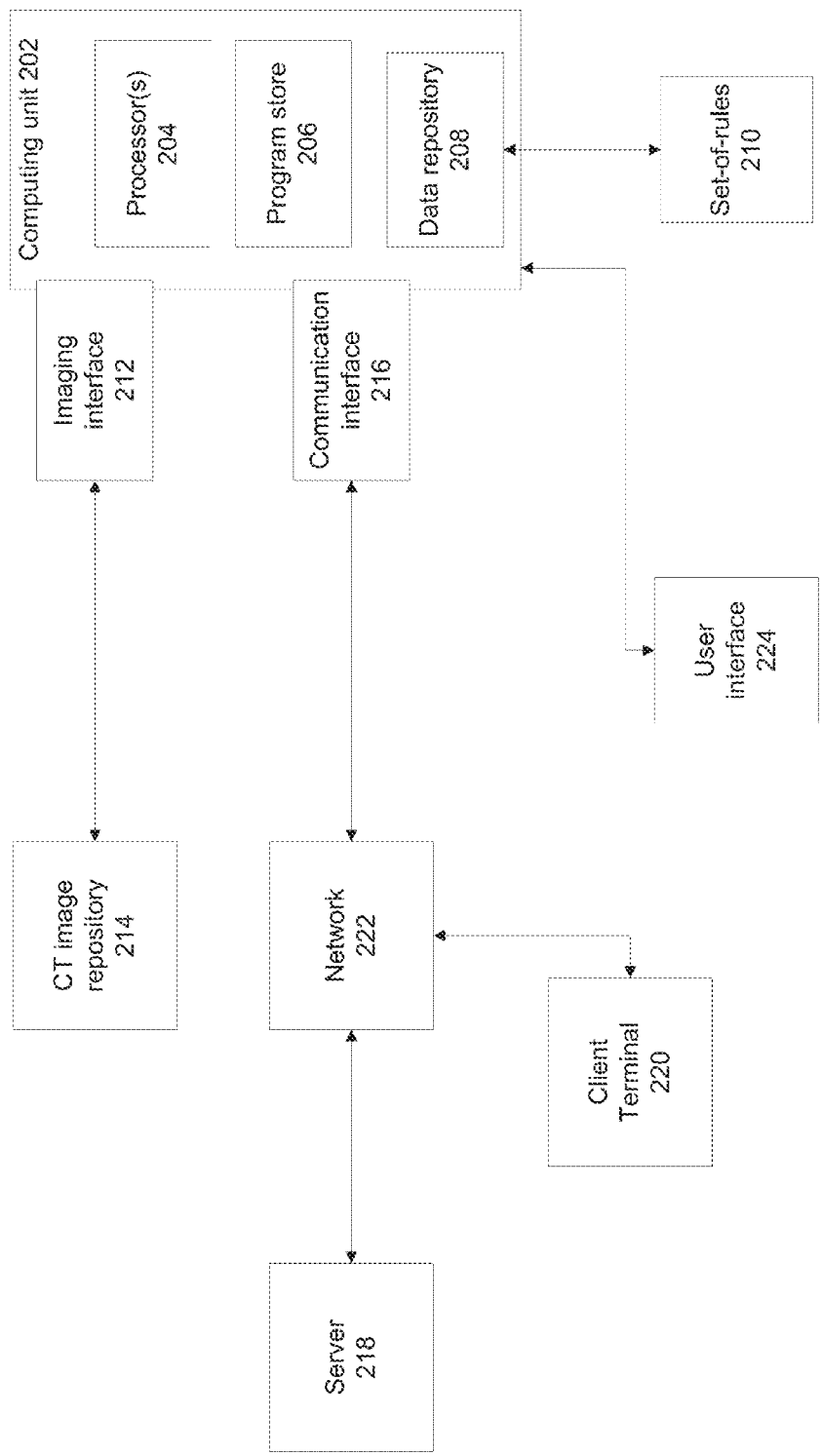
FIG. 2 is a block diagram of components of a system for automatically detecting a fatty liver from CT imaging data, in accordance with some embodiments of the present invention.

Reference is now made to FIG. 1, which is a flowchart of a computer-implemented method for automatically detecting a fatty liver (or calculates the probability of the presence of fatty liver) from CT imaging data, in accordance with some embodiments of the present invention. Reference is also made to FIG. 2, which is a block diagram of components of a system 200 that detects the fatty liver from CT imaging data, in accordance with some embodiments of the present invention. The method of FIG. 1 may be implemented by system 200 of FIG. 2.

System 200 includes a computing unit 202, for example, a server, a computer, a radiology workstation, a mobile device, a kiosk, components within an existing device, and/or a stand-alone unit.

Computing unit 202 includes a processor(s) 204, for example, a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include one or more processors (homogenous or heterogeneous), which may be arranged for parallel processing, as clusters and/or as one or more multi core processing units.

Computing unit 202 includes a program store 206 storing code instructions implementable by processor(s) 204, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Computing unit 202 include a data repository 208 storing database(s), code, and/or other data items, for example, set-of-rules 210 for identifying the fatty liver, as described herein.

Set-of-rules 210 may be stored as a file, a script, in human readable format, machine readable format, as an application programming interface (API), or other formats. Set-of-rules 210 may be a system configuration, predefined, and/or editable by a user.

Computing unit 202 includes an imaging interface 212 (e.g., physical and/or virtual interface) for communicating with a CT image repository 214 storing CT imaging data of CT scans, optionally stored based on a DICOM format. CT image repository 214 may include, for example, a Picture Archiving and Communication System (PACS) server, a CT imaging machine, a storage server, and/or other devices.

Computing unit 202 may include a communication interface 216 for communication with other devices, such as server 218 (e.g., a PACS server, a radiology workstation, a storage server, a web server), client terminal 220 (e.g., a computer, a laptop, a mobile device, a Smartphone, a Tablet, a wearable computer), optionally via a network 222 (e.g., the internet, a wireless network, a private network, a hospital network, a PACS network, a cellular network).

Computing unit 202 may include or be in communication with a user interface 224 that allows a user to enter data and/or display (and/or hear) data, for example, one or more of: a touch-screen, a display, a radiology monitor, a keyboard, a mouse, voice activated software, and a microphone.

Optionally, the acts of the method of FIG. 1 are implemented by code stored in program store 206, executed by processor 204 of computing unit 202.

At 102, imaging data of a computed tomography (CT) scan of a body of a patient is received by computing unit 202. The CT scan may be obtained from CT image repository 214 using imaging interface 212.

The imaging data may be stored using the DICOM standard.

Optionally, imaging data acquired from patients undergoing routine CT imaging (i.e., not selected for diagnosis of fatty liver) may undergo additional automatic screening analysis, such as in a by-the-way analysis routinely performed on every (or selected) acquired medical imaging data for every (or selected) patient, to detect the presence (or probability of the presence) of fatty liver. The additional screening may be performed without requiring additional significant radiologist reading time.

There may be some additional radiologist reading time, for example, to supervise the batch output and/or evaluate particular images. The patient may not require additional specialized imaging designed to screen and/or diagnose fatty liver, which may expose the patient to additional radiation. The fatty liver detection does not require dedicated scan settings, and/or additional hardware. The fatty liver detection may be performed based on existing equipment, such as by installation of code implemented using processors of existing computing units to perform the methods described herein.

The CT scan may have been ordered for a conventional clinical indication, for example, low dose CT scan of the chest to screen for lung cancer, CT scan to screen for colon cancer, standard non-contrast CT scan of the chest, intravenous (IV) contrast CT scan of the chest, standard non-contrast CT scan of the abdomen, IV contrast CT scan of the abdomen, oral contrast CT scan of the abdomen, pelvic CT scan, or other CT study protocols. The CT scan may have been ordered, for example, to help determine the cause of a bowel obstruction, to help diagnose appendicitis, assess complications of pancreatitis, screening for color cancer (i.e., virtual colonoscopy), evaluation of the urogenital system (i.e., CT urography), pre-operative work-up, or other reasons.

At 104, additional data, such as values of parameter(s) associated with the CT imaging data is received. The additional data may be extracted from metadata stored in association with the CT imaging data, such as within the images themselves, and/or within associated data, such as an electronic medical record of the patient. The additional data may be extracted from DICOM field(s) of the file storing the CT imaging data.

The use of contrast in the CT scan may be obtained. The contrast may be intravenous (IV) contrast. The imaging data may be identified as associated with a non-contrast CT (NCCT) scan or a contrast enhanced CT (CECT) scan.

The phase of the CT scan may be obtained, for example, a venous phase and/or arterial phase. The phase may be correlated with the use of contrast.

The body portion that is included in the CT scan may be obtained, for example, an abdominal scan, a chest scan, or a full body scan.

Optionally, the imaging data of the CT scan includes at least a portion of a liver (optionally the entire liver), and optionally at least a portion of a spleen.

The imaging data of the CT scan may be stored as sequentially ordered axial slices (e.g., from head to feet), for example, according to the DICOM standard.

The use of contrast or non-contrast enhanced in the CT scan of the imaging data, and/or the vascular phase of the contrast (optionally identified as arterial or venous) may be retrieved, for example, automatically from the respective DICOM file of a file storing the imaging data, from an automatic analysis of the DICOM images (e.g., image processing software that analyzes the images to detect the presence of contrast based on shapes having contrast related pixel values and/or identify the phase of contrast administration based on location of the contrast in the vasculature), and/or manually entered by a user (e.g., using a graphical user interface).

At 106, a region of the portion of the liver is segmented from the imaging data by computing unit 202. The segmentation may be performed for one or more axial slices that are identified as including the portion of the liver. The segmentation may be performed for the constructed volume.

Optionally, the segmented region of the liver (i.e., of the portion appearing in respective axial slices, and/or image volume) includes identified liver-tissue and optionally excludes non-liver tissues, for example, lung, gallbladder, blood vessels, malformations, tumors, and/or pathology. Blood vessels may be excluded from the segmented region according to a blood vessel size requirement, for example, selected to exclude the largest blood vessels in the liver, for example, the right hepatic vein, the left hepatic vein, the main hepatic vein, and the inferior vena cava.

Optionally, the segmented region is selected to include liver images from the RPS of the liver. The RPS may be selected, for example, since the RPS is expected to be more easily found in images, and/or may include larger regions of liver tissue than other areas of the liver. As described herein, the ROI used to search for the liver portion in respective axial slices (or other image formats) may be sized and/or positioned within the axial slice where the RPS is expected to be found.

Optionally, the segmentation of the region of the liver is performed based on a created binary image. The binary image may be created by code stored in program store 206 implemented by processor 204 of computing unit 202 by applying binary segmentation to a sub-set of pixels (or voxels) of the imaging data according to a second set-of-rules (e.g., script, computer instructions, code, in human and/or machine readable format). The sub-set of pixels is selected, for example, using a region of interest (ROI) positioned on the CT imaging data that includes the region of the portion of the liver. The ROI may include non-liver tissues. The second set-of-rules is designed to create the binary image that includes the region of the portion of the liver, and optionally excludes non-liver tissues. The region of the portion of the liver of the binary image is mapped to the imaging data, to designate the segmented region of the portion of the liver.

Optionally, a confidence grade that the liver region was correctly segmented is calculated. The confidence grade may be evaluated using a confidence requirement, for example, to ensure that images with high confidence grades are processed. For example, the confidence requirement may be a threshold or range, for example, above 95%, or 90%, or 80%, or other values.

Figure 3:
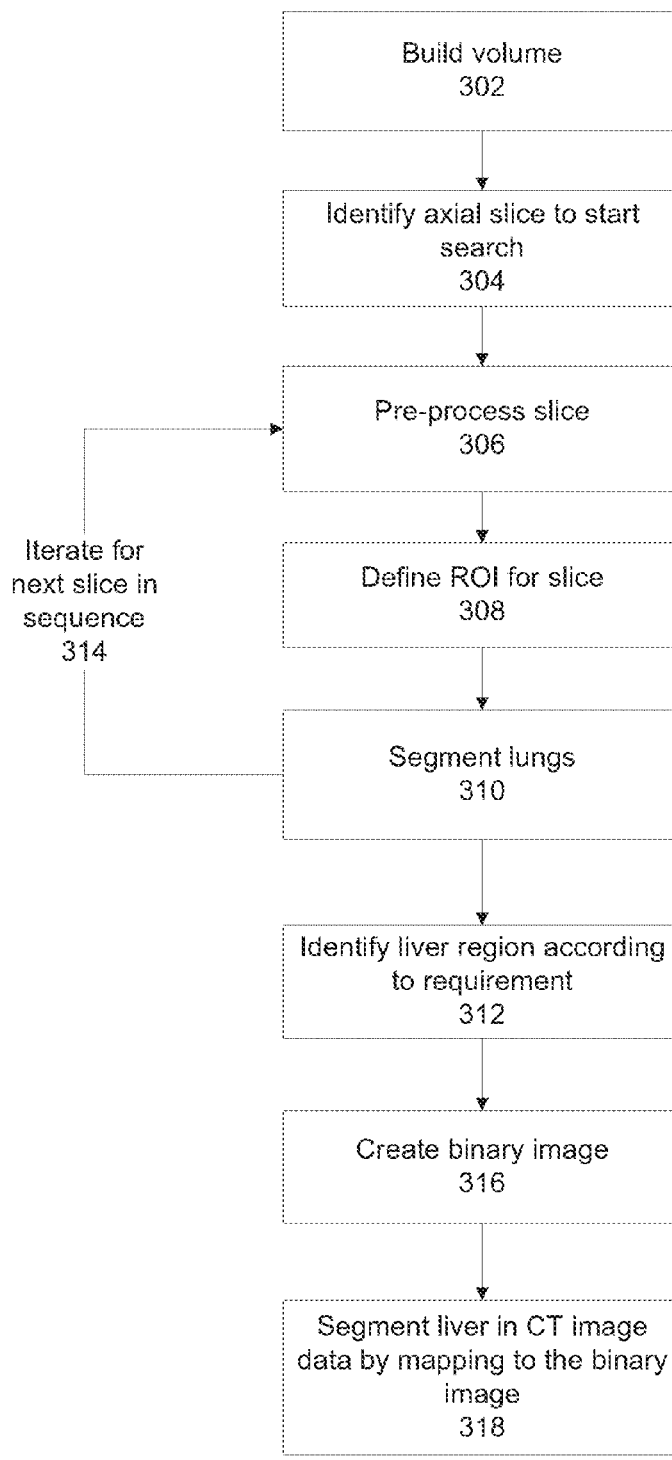
FIG. 3 is a flowchart of a computer-implemented method that segments a region of a portion of a liver, in accordance with some embodiments of the present invention.

Reference is now made to FIG. 3, which is a flowchart of a computer-implemented method that segments a region of a portion of a liver, in accordance with some embodiments of the present invention. The method may segment regions in a sub-set of CT images, for example, a sub-set of axial slices of a CT scan that include the liver. The method may segment a volume of the liver. Liver parameter(s) are calculated from the segmented region(s), as described herein. The method is designed to reduce the false positive detection rate, and/or reduce errors in detection of the liver. The method of FIG. 3 may be implemented by processor 204 of computing unit 202 implementing code instructions stored in program store 206.

At 302, a volume may be built from the imaging data, for example, from a sequence of axial slices that include pixels. Axial slices based on the DICOM standard may be positioned in order according to a patient positioning tag defined by DICOM. In cases in which the DICOM file of the CT scan does not include the correct order, when the imaging data includes slices, the actual position of the slice (according to the DICOM tag) may be considered.

The volume may be built using a predefined size for voxels.

The liver region may be segmented from one or more image slices, and/or from the volume.

At 304, an axial slice is identified from which subsequent ordered axial slices are processed for segmentation of the liver region. The axial slice is identified based on the presence of sufficient liver tissue that appears in the tissue for segmentation.

The axial slice including lung tissue may be selected for segmentation of the liver in subsequent slices, proceeding inferiorly (i.e., since the liver is located inferior to the lungs). Optionally, the axial slice is identified based on having the largest lung area from a set of sequentially organized axial slices of the imaging data.

Using the axial slice as an initial staring slice, a search for the liver region is performed in respective sequential axial slices starting from the identified axial slice in an inferior direction. Blocks 306, 308, and 310 are performed for each sequential slice. The liver may be searched for and/or segmented, for example, in every subsequent slice, or in every nth slice, for example, corresponding to ever about 8 millimeters (mm) or 10 mm, or other values. The search for the liver and/or segmentation of the liver may be performed within a defined range (selected based on the expected relative anatomical location of the liver), for example, to about 150 mm or to about 200 below the axial slice.

When the lung cannot be identified, for example, in an abdominal scan (which may be defined by the metadata and/or DICOM field in the CT imaging data), the search may be started from the first slice in the CT image set. Alternatively, when the lung cannot be identified, the method may be halted, without designation of the liver, for example, to reduce errors of detection.

At 306, the axial slice may be pre-processed. Optionally, a body portion of the patient is identified in the respective slice, for example, by identifying tissues (e.g., regions with radiation absorption) and/or excluding non-tissue regions such as the bed the patient is lying on.

The identified body portion may be eroded until the ribs (which may be identified based on shape and/or HU values of bone, and/or other methods), or until an erosion distance from the ribs, for example about 15 mm, or about 20 mm from the ribs.

At 308, the search for the liver region is performed within a ROI. The ROI is defined and/or positioned within the image and/or volume (e.g., axial image) where the liver is expected to be found, mostly posterior and within the right side of the patient. The ROI is sized and/or positioned to include at least some area of the RPS and/or other portions of the liver.

An exemplary ROI may be defined by exclusion, for example, excluding the lower 10% of the body part, excluding the upper 40% of the body part, and excluding the right 60% of the body part.

At 310, the lung within the ROI is segmented. The lung may be segmented based on pixel HU values according to a lung requirement, optionally values below −651 HU (or other values representing lung tissue, or excluding lung tissue).

At 312, the axial slice is designated for segmentation of the liver when the area of the segmented lung in the ROI is according to a liver area requirement, for example, when the area of segmented lung is below about 50% of the total ROI area, or below about 40%, or 60%, or other values. The liver is expected to be included in the other non-lung area of the ROI. The lung requirement may be selected, for example, according to the size and/or position of the ROI, to include sufficient liver tissue to allow correct segmentation of the liver.

Alternatively or additionally, the pixels of the axial slice within the ROI are analyzed for designation for segmentation of the liver using one or more parameters.

The area of lung in the image may be calculated, for example, an image with a lung area of greater than about 100 square mm located towards the front of the patient may be excluded (e.g., to make sure that the image does not include the heart, diaphragm, or a superior portion of the liver). The image within the ROI may be analyzed for the presence of bones and designated when bones are not detected (e.g., to detect whether connective tissue adhered to the liver).

Alternatively to block 312, at 314, the liver region is searched for in other axial slices by iterating boxes 306, 308, and 310. The analysis of axial slices may be performed sequentially starting from the identified axial slice in an inferior direction, in parallel, and/or using other methods.

Following block 312, at 316, a binary image is created based on the ROI, optionally for each axial slice meeting the criteria of block 312. The binary image is designed to include liver tissue (and/or to exclude non-liver tissue). The binary image may be created by calculating a histogram based on the HU values of pixels in the ROI. The histogram bins may be defined for ranges of HU values.

The HU values associated with lung tissue may be excluded. For example, the histogram is created for pixels in the range −21 HU to +150 HU, in bins of size 5 HU.

The value of the bin of the histogram having the greatest value is identified.

The binary image is created based on the ROI, by applying binary segmentation to the pixels of the ROI according to the value of the bin of the histogram having the greatest value. The binary segmentation may be performed by extending the range of the bin with greatest value by +/−10 HU. The created binary image includes the liver.

The binary image may be processed, optionally by smoothing the binary image. The smoothing may fill small holes, which may be due to acquisition noise.

At 318, the region of the liver within the image data is designated by mapping of corresponding pixels in the binary image.

The mapping may be performed using the binary pixel values within another ROI sized and positioned within the binary image. The ROI is selected to be entirely included within the liver of the binary image, such that the ROI includes only (or mostly) liver tissue. The ROI may be sized and positioned relative to the lower edge of the liver (i.e., posterior relative to the patient). When a rectangular ROI is used, the x-dimension may be defined as being about 10%-60% of the length of the lower edge of the liver, and/or a distance or range of distances relative to the lower edge of the liver. The y-dimension may be defined as a distance or range of distance relative to the lower edge of the liver, for example, about 10-30 mm above the line (i.e., anterior to the line relative to the patient). The region of the liver may be segmented by mapping the ROI defined for the binary image to the CT imaging data.

Figure 5:
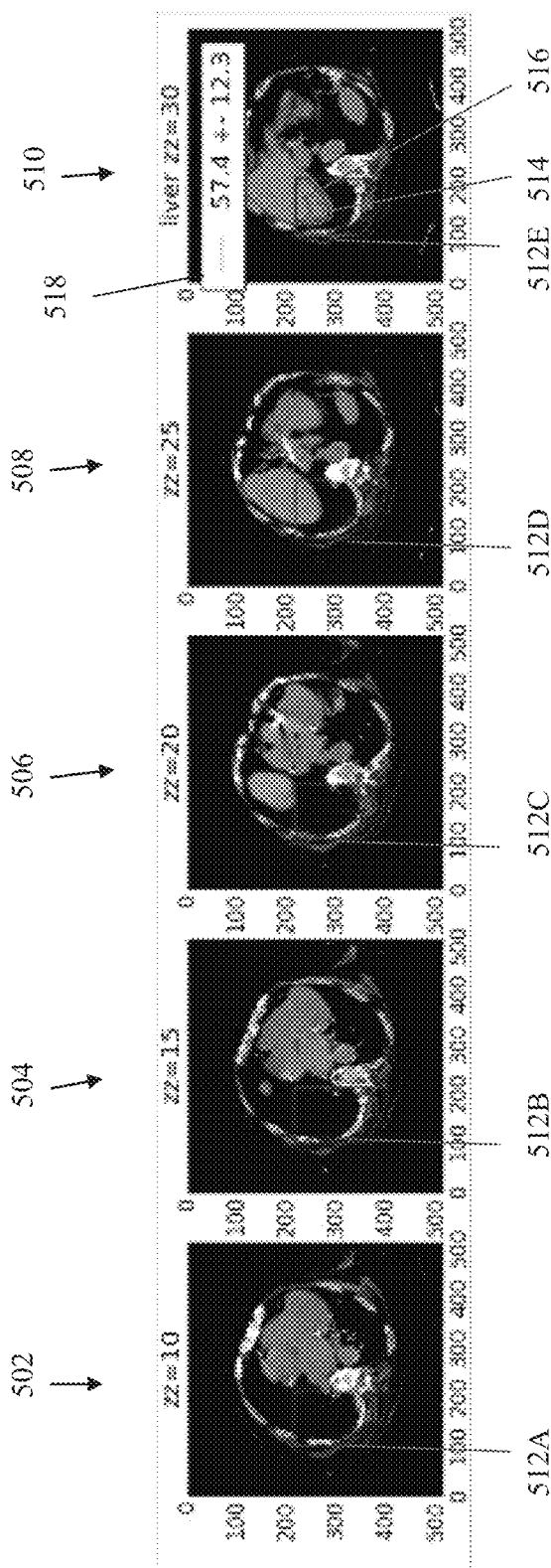
FIG. 5 is a sequence of axial CT image slices illustrating an exemplary process of segmenting a region of a liver, in accordance with some embodiments of the present invention.

Reference is now made to FIG. 5, which is a sequence of axial CT slices illustrating an exemplary process of segmenting a region of a liver according to the method described with reference to FIG. 3, in accordance with some embodiments of the present invention.

CT images 502, 504, 506, and 508 include respective ROI 512A-D used for searching for the liver. Within ROIs 512A-D, the area of lung pixels did not meet the lung requirement, since the area of lung pixels was above 50%. It is noted that the liver is not included within ROIs 512A-C, and is included within ROI 512D but with an area of less than 50%. ROI 512E of CT image 510 is processed to segment the liver. The segmented liver region is identified as area 514. The area used for calculating the liver parameter(s) (e.g., calculating the average HU value for pixels of the segmented region of the liver) is identified as area 516. Box 518 includes the liver parameter and standard deviation calculated for area 516.

Referring now back to FIG. 1, at 108, a region of a spleen may be segmented from the imaging data. An analysis of the segmented spleen may help in detection of fatty liver, for example, improve the probability of correctly detected fatty liver, as described herein.

The segmented region of the spleen may exclude tissues of other nearby organs.

The segmentation of the region of the spleen may be performed when the CT scan is identified as NCCT, or CECT in the venous phase.

Optionally, a confidence grade that the spleen region was correctly segmented is calculated. The confidence grade may be evaluated using a confidence requirement, for example, to ensure that images with high confidence grades are processed. For example, the confidence requirement may be a threshold or range, for example, above 95%, or 90%, or 80%, or other values.

Figure 4:
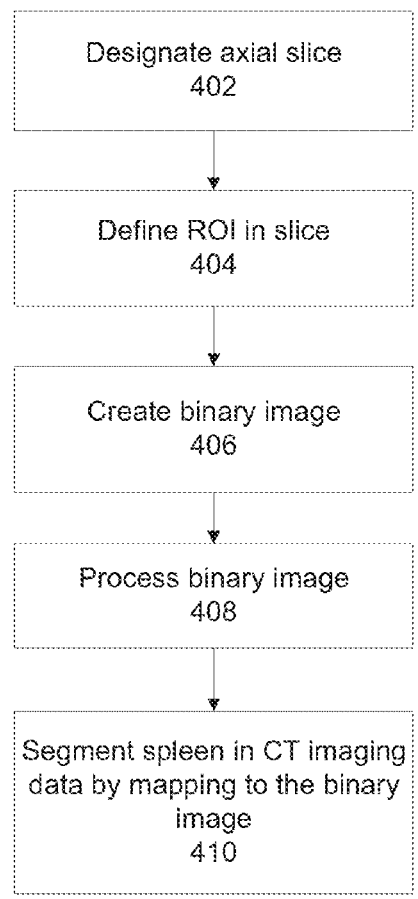
FIG. 4 is a flowchart of a computer-implemented method that segments a region of a portion of a spleen, in accordance with some embodiments of the present invention.

Reference is now made to FIG. 4, which is a flowchart of a computer-implemented method that segments a region of a portion of a spleen, in accordance with some embodiments of the present invention. The method may segment regions in a sub-set of CT images, for example, a sub-set of axial slices of a CT scan that include the spleen. The method may segment a volume of the spleen. Spleen parameter(s) are calculated from the segmented region(s), as described herein. The method is designed to reduce the false positive detection rate, and/or reduce errors in detection of the spleen. The method of FIG. 4 may be implemented by processor 204 of computing unit 202 implementing code instructions stored in program store 206.

At 402, one or more axial slices of the CT imaging data are designated for processing to segment the spleen. Optionally, the axial slices at which the liver regions are successfully segmented are designated for segmentation of the spleen.

The axial slices may be pre-processed, for example, the body part may be identified as described with reference to block 306 of FIG. 3.

At 404, an ROI is defined within the designated axial slice. The ROI is sized and/or positioned to include only or mostly spleen tissue. The ROI is positioned mostly posterior and within the left side of the patient.

An exemplary ROI may be defined by exclusion, for example, excluding the lower 10% of the body part, excluding the upper 40% of the body part, and excluding the left 60% of the body part.

At 406, a binary image is created based on the data within ROI. The binary image is created by applying binary segmentation to the pixels of the ROI. The binary segmentation is selected according to HU values selected to include spleen tissue and/or exclude non-spleen tissue (i.e., nearby organs, for example, aorta, kidney, stomach, intestines).

Optionally, the HU values used to guide the binary segmentation may be selected according to the contrast state. Optionally, when the contrast state is identified as NCCT, the range 30-60 HU is used to guide the binary segmentation for creation of the binary image.

Alternatively or additionally, the selection of HU values used to guide the binary segmentation may be selected according to the calculated liver parameter(s) (e.g., as described with reference to block 112 of FIG. 1). Optionally, a range of HU values used to guide the binary segmentation is designated as ranging from the calculated liver parameter(s) value minus 10 HU to plus 30 HU, or other values.

At 408, the created binary image may be digitally processed. The digital image processing may be selected to increase the probability of correctly segmenting the spleen. The processing may include applying a connected component method on the binary image.

Optionally, the binary image is pre-processed before connecting components.

The binary image may be pre-processed by erosion. The erosion may be selected to disconnect the spleen from other organs located nearby, which may be in contact with the spleen. The binary image may be pre-processed by dilation. The dilation may be selected to correct noisy sampling (e.g., low dose). The binarization may correct a cloud of points into a solid component.

Small components may be ignored from the component connection process, for example, components having an area of less than about 400 square mm.

The components of the binary image may be connected according to a first connection set-of-rules. An exemplary connection set-of-rules defines one or more of: a major axis within a range of 40-150 mm, a minor axis within a range of 20-100 mm, ignoring components that include air (e.g., defined by air HU values, such as less than −50 HU) which may include the stomach and intestines, ignore components with bones.

Optionally, the components are eroded.

Optionally, the largest component of the eroded components is validated according to a second connection set-of-rules. An exemplary second connection set-of-rules defines: validating that the biggest component of the eroded components is larger than half the original component size, and/or has smooth (or close to smooth) edges, that the edges fit to a second degree polynomial function with a minimum requirement, and that there are no bigger components below (i.e., posterior) or to the right (i.e., left of the patient) to avoid segmenting the stomach or intestine as the spleen.

The identified spleen component may be eroded (e.g., to avoid edges).

At 410, the region of the spleen is segmented on the CT imaging data according to the largest component, by mapping of the largest component of the binary image to corresponding pixels of the CT imaging data.

Optionally, at one or more (e.g., every) stage of the spleen search and/or segmentation a confidence grade is calculated.

Optionally, a predefined threshold (or range or other requirement) defines that the spleen detection failed or succeeded, for example, the confidence grade is below the predefine threshold.

Optionally, when the spleen detection is determined as failed, the process may continue based on liver analysis without spleen related data.

Figure 6:
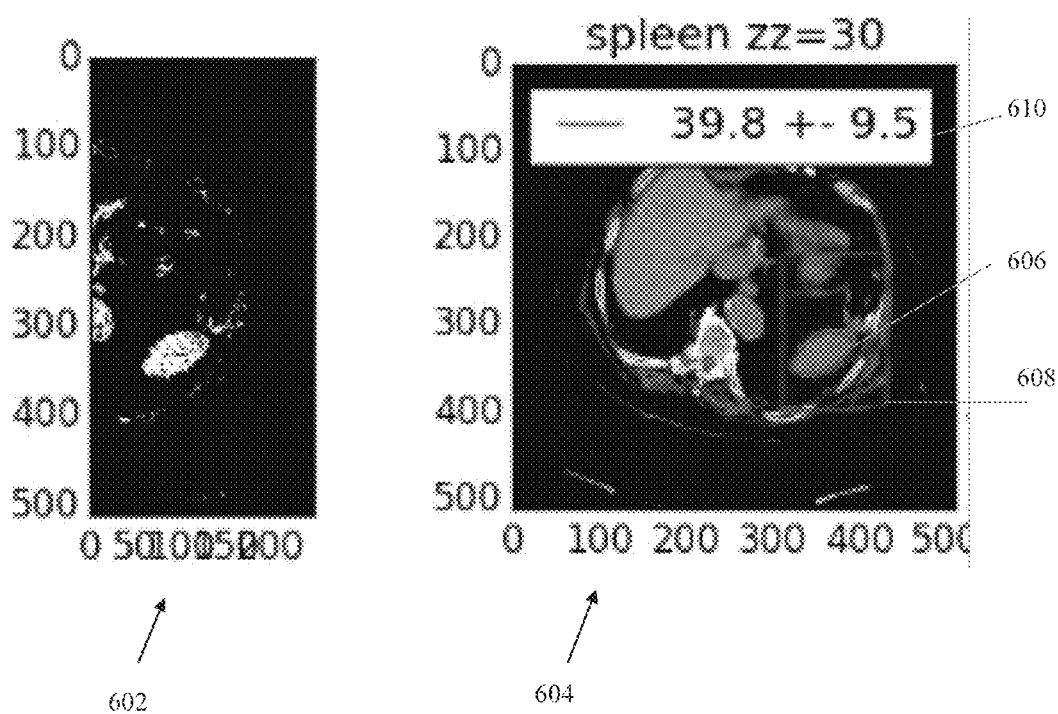
FIG. 6 includes images illustrating an exemplary process of segmenting a region of a spleen, in accordance with some embodiments of the present invention.

Reference is now made to FIG. 6, which includes images illustrating an exemplary process of segmenting a region of a spleen according to the method described with reference to FIG. 4, in accordance with some embodiments of the present invention. Image 602 is a binary image calculated from ROI 608 positioned on CT axial slice 604. Binary image 602 is created using the range 30-60 HU for binary segmentation of the pixels in ROI 608. Segmented spleen 606 is identified based on binary image 602. Segmented spleen 606 is shown after erosion. Box 610 displays the average spleen parameter and standard deviation calculated for pixels in segmented spleen 606.

Referring now back to FIG. 1, it is noted that blocks 106 and 108 may be performed sequentially, in the order of block 108 first and block 106 second, substantially simultaneously, and/or in other order and/or in parallel.

At 110, one or more spleen parameters are calculated for the segmented region of the spleen. The spleen parameters may be calculated based on HU values. The spleen parameter(s) may be calculated by averaging the HU values of pixels in the segmented region of the spleen. The spleen parameter(s) may be calculated for each axial slice, or for the set of axial slices. The spleen parameter(s) may be calculated for a volume. The standard deviation associated with the average value may be calculated.

At 112, one or more liver parameter(s) are calculated for the segmented region of the liver. The liver parameter(s) may be calculated based on HU values. Optionally, the liver parameter(s) are calculated for the segmented region of the RPS.

Optionally, the liver parameter(s) are calculated as an average value for the segmented region. The standard deviation associated with the average value may be calculated.

The liver parameter(s) may be calculated for one slice including the segmented region, multiple slices each including the segmented region, and/or for a segmented volume.

Optionally, the distribution of pixel values in the region are analyzed to detect homogeneity of HU values, for example, using a predefined normal and/or abnormal distribution, a set-of-rules, and/or trained machine learning algorithm. Abnormal distributions, such as large variations in HU values of pixels in proximity to one another, and/or variations within the region may be indicative of non-homogeneity in the liver, for example, hemangioma, tumors, or other pathologies. Optionally, a very low liver density (e.g., relative to a low liver density requirement, for example, less than 20 HU) may suggest an abnormality such as a very big hemangioma, cysts or pleural fluid. A non-homogenous liver density may indicate a hemangioma or other abnormality. In such a case, in block 116, the indication of a possible abnormality may be generated.

Optionally, the segmented region of the liver is evaluated using quality criteria, which is selected to help determine whether the segmentation correctly includes liver tissue or not. The quality criteria may be a threshold or range that defines pixel values for liver tissue, for example, 10 HU. Calculated liver parameter(s) not meeting the quality criteria may suggest an incorrect segmentation, for example, a segmentation of pleural fluid from the thorax, hemangioma, abnormalities in the liver, or other non-liver tissue. The quality criteria may be applied per axial slice, to include axial slices with correctly segmented liver and/or exclude slices with incorrect segmentation of the liver.

Optionally, the quality criteria is used for calculation of the confidence grade of the output. Optionally, the confidence grade is evaluated using predefined parameters based on the measurement results and validation of prior results.

Optionally, the confidence grade is related to a predefined requirement (e.g., threshold, range). For example, when the confidence grade value is below the threshold value, the segmentation process is marked as failed.

Optionally, the output of the process may include an image (with the slice(s) where the liver is detected. The image may also include mark of the ROI where average value is calculated based on that slice.

Figure 7:
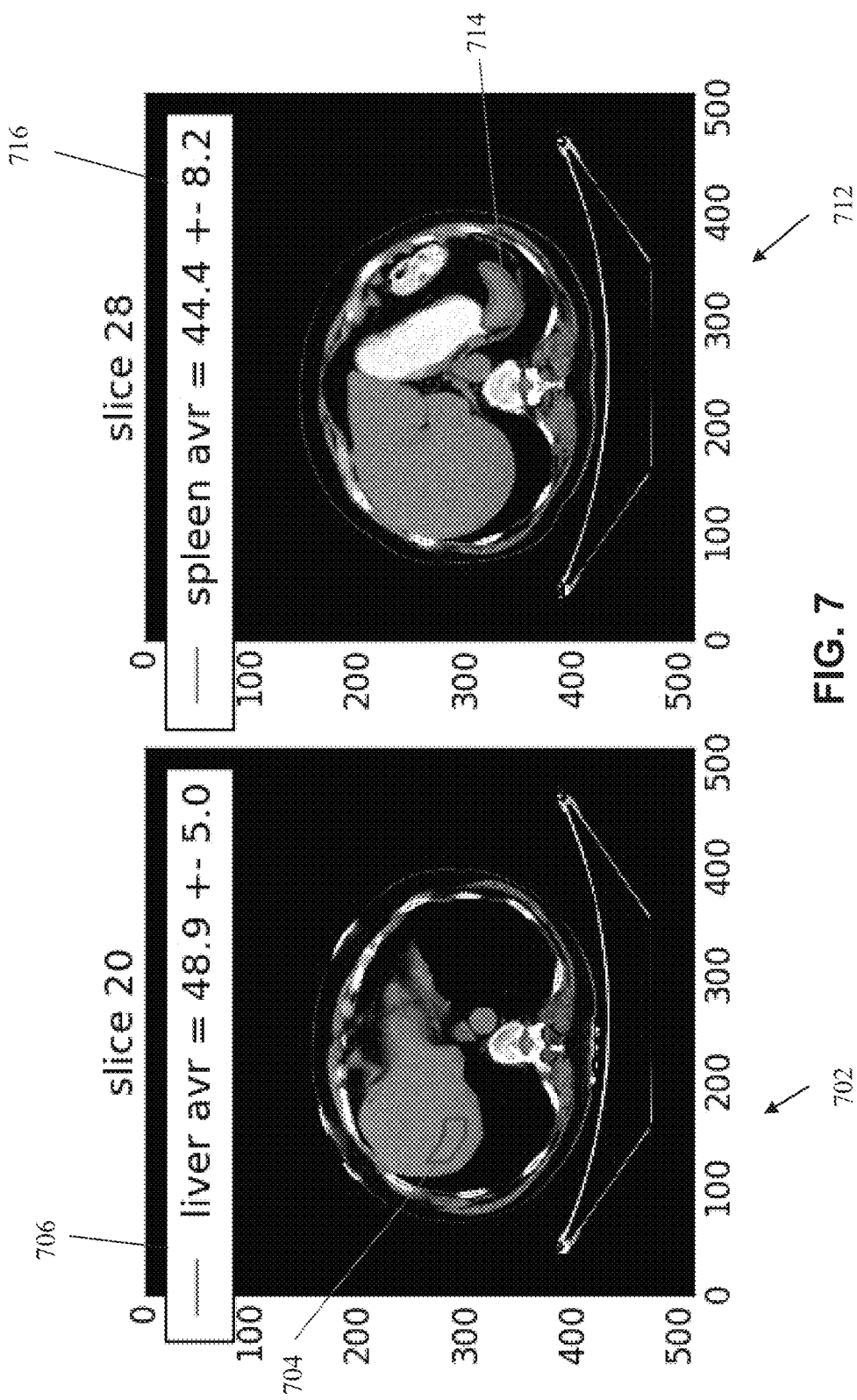
FIG. 7 is an exemplary output of CT axial images including marking of the ROI used to find the liver region and/or spleen region for calculation of the liver parameter and/or spleen parameter, in accordance with some embodiments of the present invention.

Reference is now made to FIG. 7, which is an exemplary output of CT axial images including marking of the ROI used to find the liver region and/or spleen region for calculation of the liver parameter and/or spleen parameter, in accordance with some embodiments of the present invention. Image 702 depicts axial slice 20, including marking 704 depicting the ROI used to calculate the liver parameter (presented in box 706). Image 712 depicts axial slice 28, including marking 714 depicting the ROI used to calculate the spleen parameter (presented in box 716).

Referring now back to FIG. 1, at 114, the presence of a fatty liver is determined by analyzing the calculated liver HU value(s) according to a set-of-rules.

Optionally, the presence of the fatty liver is determined by analyzing the calculated liver parameter(s) in view of the calculated spleen parameter(s) according to the set-of-rules.

Optionally, the set-of-rules include instructions to detect the fatty liver when the liver parameter(s) are below a threshold of 40 HU in association with the use of contrast or non-contrast imaging.

Alternatively or additionally, the set-of-rules include instructions to detect the fatty liver when the calculated liver parameter(s) are at least 10 HU below the calculated spleen parameter(s), when the CT images are not acquired during the arterial phase of an IV contrast enhanced scan.

Alternatively or additionally, the set-of-rules may not cover all the range of optional liver and/or spleen parameters and may include ranges of unknown (e.g., diagnosis).

The set-of-rules may be selected to obtain a high sensitivity for identification of fatty liver, for example, at least about 80%, or 90%, or other values. It may be desirable to try to identify all cases of fatty liver with the cost of falsely identifying non-fatty liver as fatty liver (e.g., since the error in automatic detection may be corrected with further investigation), rather than missing cases of actual fatty liver (e.g., since early detection may prevent medical complications).

Optionally, the probability of correctly detecting the fatty liver is calculated.

The probability calculation may be performed based on the set-of-rules, for example, different single or combinations of rules that are satisfied may be associated with a probability value.

At 116, an indication including the presence of the fatty liver is outputted. The indication may include the confidence grade of the segmentation and/or the probability of fatty liver. The indication may be stored locally, remotely, and/or in CT image repository 214, for example, within metadata associated with the CT imaging data, within an electronic medical record of the patient, within a DICOM field associated with the CT imaging data, and/or in an event log. The indication may be transmitted using communication interface 216 for display on client terminal 220, and/or displayed on user interface 224.

The indication may include markings (e.g., lines, tags, coloring) of the segmented region on each respective axial slice of the imaging data where the liver and/or spleen were successfully segments (for example, as shown in FIG. 7, discussed above). The indication may include markings (e.g., lines, boxes, tags, coloring) of the ROI used on each respective axial slice of the imaging data to search for the region of the liver and/or spleen. The indication may include instructions, to output the CT imaging data including the axial slices with markings for presentation on a display (e.g., of client terminal 220 and/or user interface 224).

The indication may include the presence of fatty liver in the CT image data.

The indication may include the absence of fatty liver. The indication may include a calculated probability of the presence of fatty liver. The indication may be unknown when there is no rule to define (e.g., diagnose) the parameter (e.g., average value) as fatty liver or normal.

The indication may include the calculated liver parameter(s) and optionally the spleen parameter(s).

The indication may include statistical information of large scale population and the patient's liver (and optionally the spleen) average values (for example, as discussed with reference to FIG. 8 below). The statistics may be presented as a histogram or as scale range, or other formats. The statistics may be for relevant populations or for part of the population according to parameter such as demographics or related to the scan parameters.

When abnormalities in the liver are detected, the indication may include the detected abnormality, for example, as a message recommending that further investigation may be required.

The indication may be used to flag (manually and/or automatically) patients, which may be at high risk of cardiovascular or metabolic events. The flagged patients may be sent for further work-up (manually and/or automatically). The indication may be used as a wake-up call to patients to spur lifestyle interventions and/or other preventive treatment, which may reverse the fatty liver and/or related conditions (e.g., pre-diabetes), for example, by a change in diet, exercise, and reduced alcohol intake.

Inventors designed an experiment to test the ability of systems and/or methods described herein to identify fatty liver in CT scans of patients. A total of 8284 CT scans were included. Overall, the systems and/or methods successfully processed 7766 CT scans (93.7%), and failed to complete processing of the other 518 (6.3%).

The 7766 CT scans that were successfully processed represent a wide variation in patient demographics. In terms of age, the minimum age was 20 years, the maximum was 97 years, the average 66.1 years, and the standard deviation was 11.7. 6042 (77.8%) were female and 1724 (22.2%) were male. 4684 (60.3%) of the CT scans were enhanced with IV contrast, 1677 (21.6%) did not include IV contrast, and in 1405 (18.1%) the use of contrast was unknown. The average value of the calculated liver parameter(s) (average HU value) for the CT scans was 71.2 with a standard deviation of 24.5. The spleen was identified and used in the process of identifying the fatty liver in 2672 of the non-contrast CT scans. The average value of the calculated spleen parameter(s) (average HU value) for the CT scans was 45.4 with a standard deviation of 6.2. A randomly selected sample of 500 CT scans showed that the rate of incorrect segmentation of the liver was less than 1%, and the rate of incorrect segmentation of the spleen was less than 4%.

Figure 8:
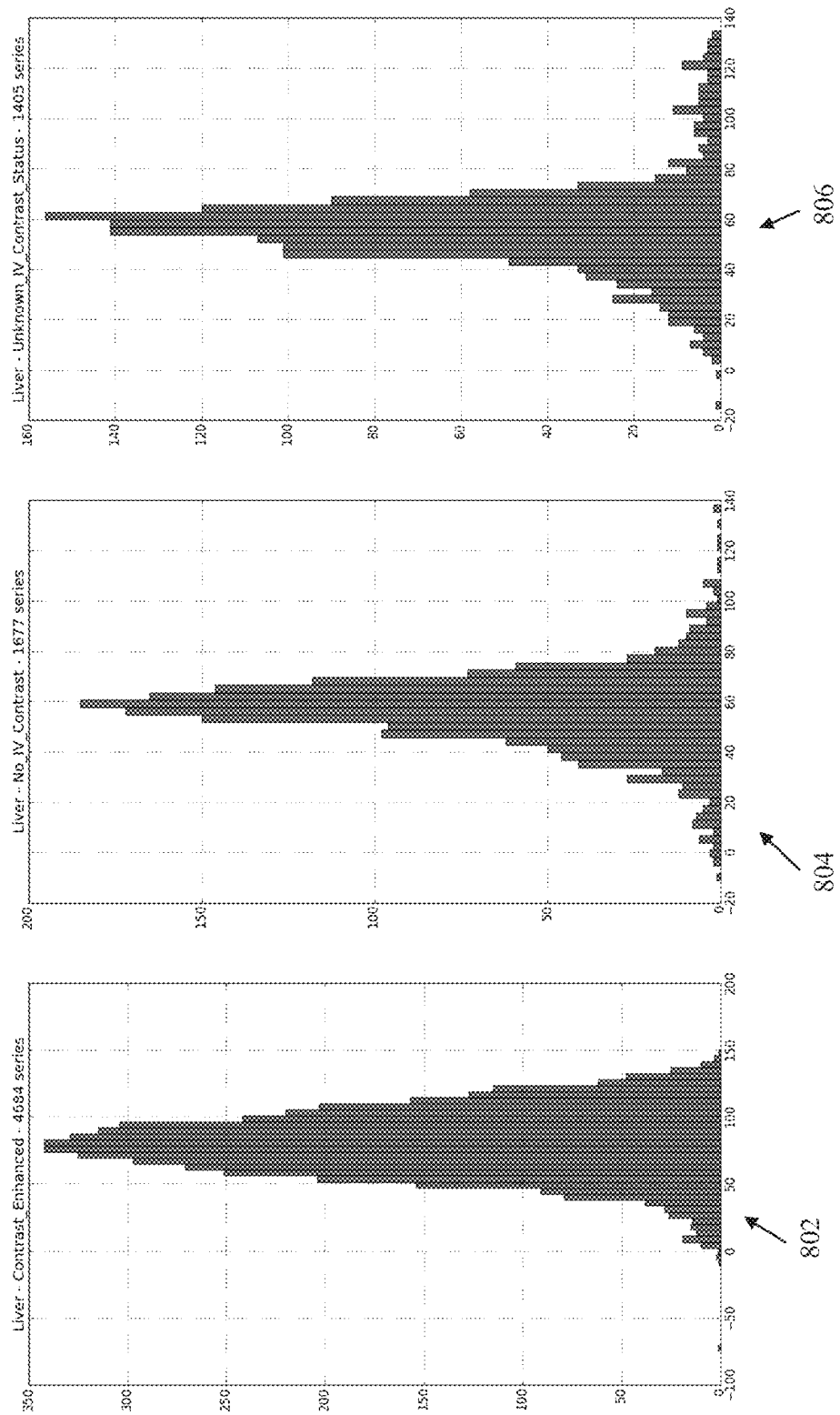
FIG. 8 includes histograms presenting results of an experiment, in accordance with some embodiments of the present invention.

Reference is now made to FIG. 8, which includes histograms presenting results of the experiment, in accordance with some embodiments of the present invention. The x-axis of the histograms depicts the calculated average liver density for the population represented by the respective histogram. The y-axis depicts the number of samples. Histogram 802 depicts results for the contrast enhanced series, histogram 804 depicts results for the no-contrast series, and histogram 806 depicts results for the contrast unknown series.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant imaging data formats for storing CT images will be developed and the scope of the term imaging data is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer-implemented method for detecting a fatty liver from CT imaging data, comprising:
   receiving imaging data of a computed tomography (CT) scan of a body of a patient including at least a portion of a liver, the CT scan performed using a single source CT Scanner with settings selected for imaging of non-fatty-liver pathology;
   segmenting at least a region of the portion of the liver from the imaging data by creating a binary image by applying binary segmentation to a sub-set of pixels of the imaging data according to a first set-of-rules, wherein the binary image includes the region of the portion of the liver, and mapping the region of the portion of the liver of the binary image to the segmented region of the portion of the liver of the imaging data;
   calculating at least one liver parameter for the segmented region of the liver from Hounsfield unit (HU) value(s);
   detecting the presence of a fatty liver by analyzing the calculated at least one liver parameter according to a second set-of-rules; and
   outputting an indication of the presence of the fatty liver.

2. The method of claim 1, further comprising calculating a probability of correctly identifying the presence of the fatty liver, and outputting the probability in association with the indication.

3. The method of claim 1, further comprising calculating a confidence grade of correctly segmenting at least one of the liver region and a spleen region.

4. The method of claim 1, further comprising:
   identifying that the imaging data is associated with a non-contrast CT (NCCT) scan or a venous phase of a contrast enhanced CT (CECT) scan;
   segmenting a region of a spleen from the imaging data;
   calculating at least one spleen parameter for the segmented region of the spleen; and
   detecting the presence of the fatty liver by analyzing the calculated at least one liver parameter in view of the calculated at least one spleen parameter according to the second set-of-rules.

5. The method of claim 4, wherein the second set-of-rules comprises detecting the fatty liver when the at least one liver parameter includes an average HU at least 10 HU below the at least one spleen parameter including an average of HU values.

6. The method of claim 4, wherein the identifying of the imaging data associated with non-contrast or contrast enhanced and the vascular phase of contrast identified as arterial or venous is retrieved from a respective DICOM field of a file storing the imaging data.

7. The method of claim 4, wherein the identifying of the imaging data associated with non-contrast or contrast enhanced and the vascular phase of contrast identified as arterial or venous is retrieved using an automatic analysis of the DICOM images.

8. The method of claim 4, wherein the identifying of the imaging data associated with non-contrast or contrast enhanced and the vascular phase of contrast identified as arterial or venous is received as manually entered input.

9. The method of claim 4, wherein segmenting the region of the spleen further comprises excluding tissues of other nearby organs from the segmentation.

10. The method of claim 4, further comprising:
    designating an axial slice at which the liver region has been segmented from a set of sequentially organized axial slices of the imaging data; and
    wherein segmenting comprises segmenting the region of the spleen from the designated axial slice.

11. The method of claim 10, further comprising:
    defining an ROI within the designated axial slice positioned mostly posterior and within the left side of the patient;
    creating a binary image based on the ROI by applying binary segmentation to the pixels of the ROI according to at least one of: predefined HU values when the imaging data is associated with CT image acquisition, and relative to the calculation of least one liver parameter; and
    mapping the region of the spleen within the image data according to corresponding pixels in the binary image.

12. The method of claim 11, further comprising:
pre-processing the binary image by at least one of erosion and dilation;
connecting components of the binary image according to a first connection set-of-rules;
validating the largest component according to a second connection set-of-rules; and
mapping the region of the spleen according to the largest component.

13. The method of claim 1, wherein the second set-of-rules comprise detecting the fatty liver when the at least one liver parameter is below a threshold of 40 HU.

14. The method of claim 1, wherein segmenting the portion of the liver comprises segmenting tissue of the portion of the liver and excluding blood vessels from the segmentation according to a blood vessel size requirement.

15. The method of claim 1, wherein segmenting comprises segmenting the region within the right posterior sector (RPS), and wherein calculating comprises calculating the at least one liver parameter for the segmented region of the RPS.

16. The method of claim 1, further comprising building a volume from the imaging data using a predefined size for voxels, and segmenting comprises segmenting the region from the volume.

17. The method of claim 1, further comprising identifying an axial slice having the largest lung area from a set of sequentially organized axial slices of the imaging data, and searching for the liver region in respective sequential axial slices starting from the identified axial slice in an inferior direction.

18. The method of claim 17, wherein the search is performed within a region of interest (ROI) positioned mostly posterior and within the right side of the patient.

19. The method of claim 18, further comprising, for each respective axial slice in the sequence:
identifying a body portion of the patient;
eroding the body portion until the ribs or until an erosion distance from the ribs;
defining the ROI within the respective axial slice;
segmenting the lungs within the ROI according to HU values of pixels according to a lung requirement; and
identifying the region of the liver when the area of the segmented lung in the ROI is according to a liver area requirement.

20. The method of claim 19, wherein identifying the region of the liver further comprises:
calculating a histogram based on the HU values of pixels in the ROI;
creating a binary image based on the ROI by applying binary segmentation to the pixels of the ROI according to the value of the bin of the histogram having the greatest value; and
mapping the region of the liver within the image data according to corresponding pixels in the binary image.

21. The method of claim 20, wherein mapping further comprises mapping the region of the liver based on the binary image such that the region is located a distance from the edge of the liver, within the liver.

22. A system for detecting a fatty liver from CT imaging data, comprising:
an imaging interface for receiving imaging data of a CT scan of a body of a patient including at least a portion of a liver acquired by a single source CT scanner with settings selected for imaging of non-fatty liver pathology;
a communication interface for communicating with an external device;
a program store storing code; and
a processor coupled to the imaging interface, the communication interface, and the program store for implementing the stored code, the code comprising:
code to receive, using the imaging interface, imaging data of a computed tomography (CT) scan of a body of a patient including at least a portion of a liver;
code to segment at least a region of the portion of the liver from the imaging data, by creating a binary image by applying binary segmentation to a sub-set of pixels of the imaging data according to a first set-of-rules, wherein the binary image includes the region of the portion of the liver, and mapping the region of the portion of the liver of the binary image to the segmented region of the portion of the liver of the imaging data;
code to calculate at least one liver parameter for the segmented region of the liver based on HU values, detect the presence of a fatty liver by analyzing the at least one calculated liver parameter according to a second set-of-rules; and
code to output an indication of the presence of the fatty liver using the communication interface.

23. The system of claim 22, further comprising:
code to mark the segmented region on a respective axial slice of the imaging data, and code to output the respective axial slice for presentation on a display.

24. A computer program product comprising a non-transitory computer readable storage medium storing program code thereon for implementation by a processor of a computing unit that detects a fatty liver from CT imaging data, the program code comprising:
instructions to receive imaging data of a computed tomography (CT) scan of a body of a patient including at least a portion of a liver, the CT scan performed using a single source CT Scanner with settings selected for imaging of non-fatty-liver pathology;
instructions to segment at least a region of the portion of the liver from the imaging data by creating a binary image by applying binary segmentation to a sub-set of pixels of the imaging data according to a first set-of-rules, wherein the binary image includes the region of the portion of the liver, and mapping the region of the portion of the liver of the binary image to the segmented region of the portion of the liver of the imaging data;
instructions to calculate at least one liver parameter for the segmented region of the liver based on HU values;
instructions to detect the presence of a fatty liver by analyzing the calculated at least one liver parameter according to a second set-of-rules; and
instructions to output an indication of the presence of the fatty liver.

* * * * *